(12) United States Patent
Persson

(10) Patent No.: US 9,010,319 B2
(45) Date of Patent: Apr. 21, 2015

(54) METHOD AND DEVICE FOR SUPPORTING AND RETAINING MEDICAL APPLIANCES

(75) Inventor: Jan-Ove Persson, Höör (SE)

(73) Assignee: Atos Medical AB, Horby (SE)

( * ) Notice: Subject to any disclaimer, the term of this patent is extended or adjusted under 35 U.S.C. 154(b) by 1012 days.

(21) Appl. No.: 12/531,390

(22) PCT Filed: Apr. 11, 2008

(86) PCT No.: PCT/SE2008/050417
§ 371 (c)(1),
(2), (4) Date: Sep. 15, 2009

(87) PCT Pub. No.: WO2008/127189
PCT Pub. Date: Oct. 23, 2008

(65) Prior Publication Data
US 2010/0101582 A1    Apr. 29, 2010

(30) Foreign Application Priority Data
Apr. 12, 2007  (SE) ................. 2007/000343

(51) Int. Cl.
*A61M 16/00*   (2006.01)
*A62B 9/02*   (2006.01)
(Continued)

(52) U.S. Cl.
CPC .......... *A61M 16/0488* (2013.01); *A61M 16/047* (2013.01); *A61M 16/0497* (2013.01);
(Continued)

(58) Field of Classification Search
CPC .......... A61M 16/047; A61M 16/0465; A61M 16/0497; A61M 16/0463; A61M 25/02; A61M 2025/0206; A61M 2025/0253; A61M 2025/026; A61M 2025/0266

USPC .......... 128/207.14, 207.17, 200.26, 912, 136, 128/207.29, 205.22; 604/174, 175, 180, 604/176, 178, 179
See application file for complete search history.

(56) References Cited

U.S. PATENT DOCUMENTS 3,585,997 A * 6/1971 Ancerewicz, Jr. ............ 604/327
3,677,250 A * 7/1972 Thomas ........................ 604/180
(Continued)

FOREIGN PATENT DOCUMENTS

DE    29806659 U1    7/1998
EP    1477197 A1    5/2004
(Continued)

OTHER PUBLICATIONS

"PCT International Search Report dated Jul. 2, 2008 for PCT/SE2008/050417, from which the instant application is based," 5 pgs.
(Continued)

*Primary Examiner* — Lynne Anderson
*Assistant Examiner* — Bradley Philips
(74) *Attorney, Agent, or Firm* — Fredrikson & Byron, P.A.

(57) ABSTRACT

A device (11) for supporting and retaining medical appliances (10), such as tracheal cannulas and stoma stents, in the neck of a patient comprising supporting means (12) for supporting and retaining the medical appliance (10) and fastening means (13) for fastening the device on the body (36) of a patient. The fastening means (13) is provided at a distance from the supporting means and comprises means for attaching the device to the chest (36) of the patient. A method for supporting and retaining medical appliances (10), such as tracheal cannulas and stoma stents, in the neck of a patient, by fastening the appliance (10) on the body (36) of a patient outside the neck.

13 Claims, 4 Drawing Sheets

(51) Int. Cl.
*A62B 9/06* (2006.01)
*A61M 16/04* (2006.01)
*A61B 17/84* (2006.01)
*A61M 25/02* (2006.01)

(52) U.S. Cl.
CPC ............... *A61B17/84* (2013.01); *A61M 16/04* (2013.01); *A61M 25/02* (2013.01); *A61M 2025/0266* (2013.01); *A61M 2209/08* (2013.01); *A61M 2210/10* (2013.01)

(56) References Cited

U.S. PATENT DOCUMENTS

| | | | |
|---|---|---|---|
| 4,331,144 A | 5/1982 | Wapner | |
| 4,489,723 A | 12/1984 | Simons et al. | |
| 4,516,293 A * | 5/1985 | Beran | 24/16 PB |
| 4,574,798 A | 3/1986 | Heitzman | |
| 4,772,261 A * | 9/1988 | Von Hoff et al. | 604/507 |
| 4,891,846 A * | 1/1990 | Sager et al. | 2/48 |
| 4,988,338 A * | 1/1991 | Taylor et al. | 604/180 |
| 5,000,741 A * | 3/1991 | Kalt | 604/180 |
| 5,058,579 A * | 10/1991 | Terry et al. | 128/207.14 |
| 5,163,914 A | 11/1992 | Abel | |
| 5,471,980 A | 12/1995 | Varner | |
| 5,558,090 A | 9/1996 | James | |
| 5,626,565 A | 5/1997 | Landis et al. | |
| 5,672,159 A * | 9/1997 | Warrick | 604/179 |
| 5,749,360 A * | 5/1998 | Lacey et al. | 128/207.14 |
| 5,918,599 A * | 7/1999 | Shesol | 128/207.17 |
| 5,924,421 A * | 7/1999 | Rosbrook et al. | 128/207.14 |
| 6,117,163 A | 9/2000 | Bierman | |
| 6,186,139 B1 * | 2/2001 | Bezicot et al. | 128/200.24 |
| 6,571,395 B1 * | 6/2003 | Korkor | 2/45 |
| 7,247,150 B2 * | 7/2007 | Bierman | 604/174 |
| 8,347,881 B2 * | 1/2013 | Tanaka et al. | 128/200.24 |
| 2004/0226564 A1 * | 11/2004 | Persson | 128/207.14 |
| 2009/0306603 A1 * | 12/2009 | Bierman et al. | 604/180 |
| 2010/0179481 A1 * | 7/2010 | Bierman et al. | 604/177 |

FOREIGN PATENT DOCUMENTS

| | | |
|---|---|---|
| EP | 1454601 A2 | 9/2004 |
| GB | 2244924 A | 12/1991 |
| WO | 9006735 A1 | 6/1990 |

OTHER PUBLICATIONS

"PCT Written Opinion dated Jul. 2, 2008 for PCT/SE2008/050417, from which the instant application is based," 6 pgs.

"PCT International Search Report dated Jun. 13, 2007 for PCT/SE2007/000343," 4 pgs.

* cited by examiner

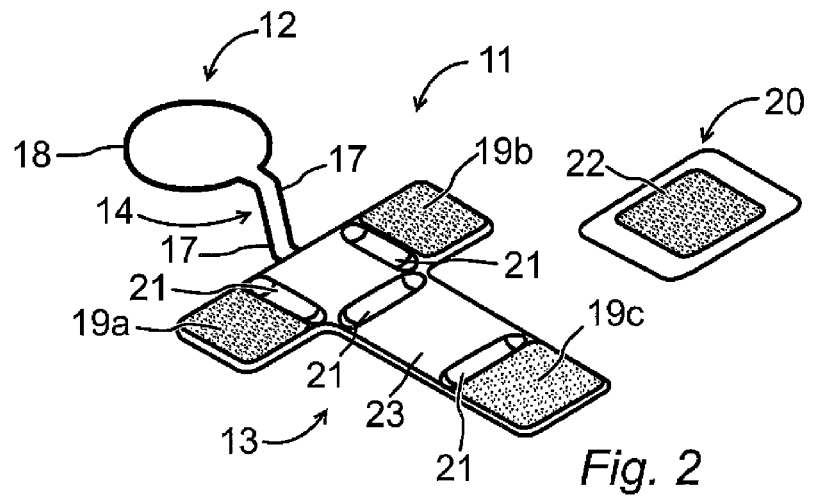
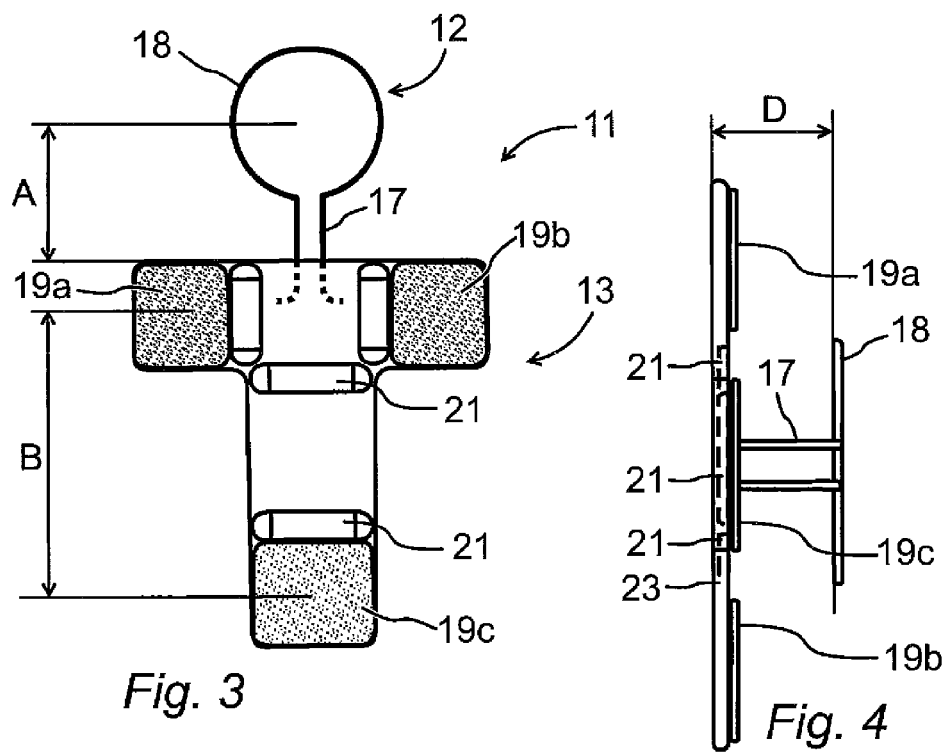

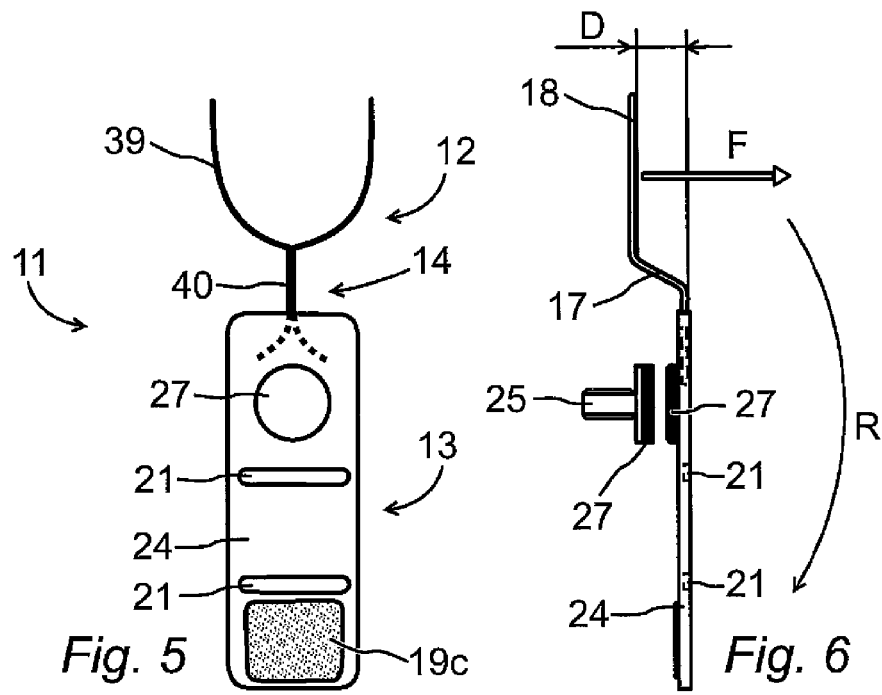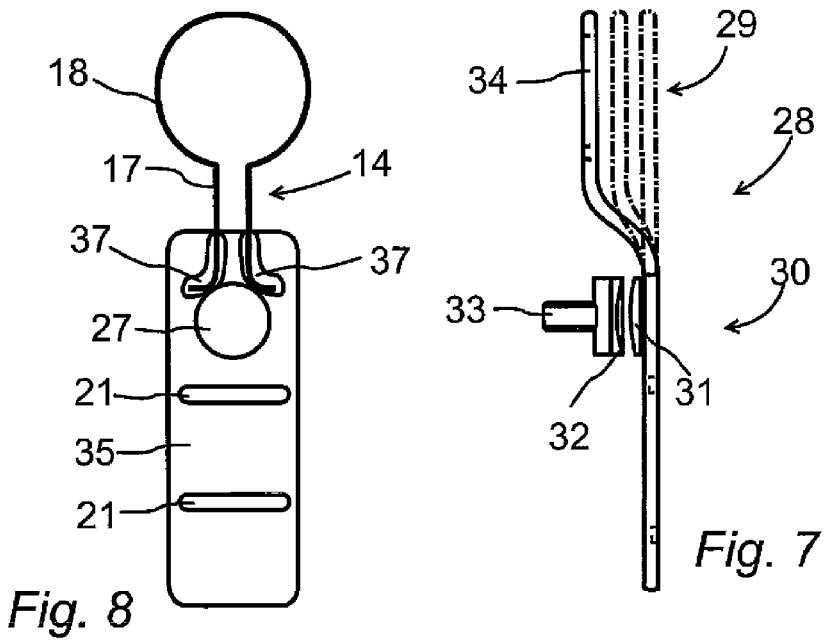

METHOD AND DEVICE FOR SUPPORTING AND RETAINING MEDICAL APPLIANCES

RELATED APPLICATIONS

This application is a 35 U.S.C. 371 national stage filing from International Application No. PCT/SE2008/050417 filed Apr. 11, 2008 which claims priority to International Application No. PCT/SE2007/000343 filed Apr. 12, 2007, the teachings of which are incorporated herein by reference.

TECHNICAL FIELD

The invention relates to a device for supporting and retaining a tracheal cannula or similar appliance on a person's neck in connection with tracheotomy. Some conditions where a tracheotomy may be used are in acute settings, such as maxillofacial injuries, large tumors of the head and neck, congenital tumors, e.g. branchial cyst, acute inflammation of head and neck. A tracheotomy also can be used in chronic/elective settings when there is need for long term mechanical ventilation and tracheal toilet, e.g. comatose patients, surgery to the head and neck. A laryngectomy is the most common surgery used for the treatment of laryngeal cancer. In the operation, the larynx (and with it the vocal cords, etc.) is removed completely. Other causes for a surgical procedure of this kind can be a physical injury against the neck in an accident, sleep apnea of overweight persons, and lung diseases.

When performing a tracheotomy or laryngectomy a hole in the neck is created. This hole is called a tracheostoma, or more generally a stoma, permitting the patient to breathe through it after the surgery. The air is passed from outside through the tracheostoma directly to the lungs without passing through the upper airways.

PRIOR ART

On tracheostomized persons it is necessary to keep the stoma open. Normally a tracheal cannula is used. Different embodiments of tracheal cannulas are disclosed in U.S. Pat. No. 5,471,980, U.S. Pat. No. 4,331,144 and DE29806659. The tracheal cannula is exposed to axial forces, which particularly at coughing and speech tend to cause outward movement of the cannula in the stoma causing irritation of mucous membranes and leakage. In worst case the cannula may be pressed completely out of the stoma. A device specifically designed for improved stability is disclosed in EP1454601. The device comprises a flat base with one curved side pointing upwards towards the chin of the user and three rounded corners, used for attaching the base to the neck of the patient with an elastic band and a strip of adhesive tape.

In order to keep the cannula in position it can be held by means of a neck strap which can be of different types varying from simple cotton straps which are connected with the cannula and are tied round the neck by a knot. More sophisticated and advanced straps are disclosed e.g. in U.S. Pat. No. 5,471,980 and U.S. Pat. No. 4,331,144.

Most patients that are subject to tracheotomy or laryngectomy suffer from a very fragile and sensitive skin around the stomal site or wound area. A disadvantage with prior art fixation devices is that they tend to irritate the skin. Prior art devices are clearly visible in use which is considered to be a drawback by most patients. The handicap is experienced as very embarrassing and there is a desire for a more discreet device.

To some extent cosmetic improvements are present in a tracheostomy dressing as disclosed in U.S. Pat. No. 5,058,579. The dressing comprises an occlusive adhesive-backed dressing, a means for securing a tracheostomy tube to the adhesive dressing and a means for attaching an absorbing pad. Even though improvements are made there is a need for a device that will be experienced as less conspicuous than prior art devices.

SUMMARY OF THE INVENTION

An object of the present invention is to overcome drawbacks and disadvantages of prior art devices and to provide a device for supporting and retaining medical appliances that will be more easily concealed by a user than prior art devices. The device also will ensure that fragile and sensitive skin around the stomal site or wound area is not irritated or further damaged. The device is secured to the body below the stomal site at a distance which normally is sufficient for preserving the sensitive or damaged portion of the skin.

The device comprises a supporting means for supporting and retaining the medical appliance and fastening means for fastening the device on the body of a patient or person. The fastening means can be divided into a body attached element and a connecting element. The connecting element is provided on a holder or base plate. The body attached element is secured to the chest and ensures that no straps or further means are required to keep the device engaged to the body. This design also will allow removal of the holder including the supporting means while leaving the fastening means firmly attached to the body.

A further advantage with the device in accordance with the invention is that the device will not be moved when the head is turned. As a result the tissue around and/or inside the stoma will not be affected or further irritated. Still a further advantage is that leakage around the appliance will be prevented.

In one embodiment in accordance with the invention the fastening means is provided with a first fastener and a second fastener or stabilising means, the second fastener being located further away from the supporting means than the first fastener. As a result the device is prevented from rotating around the first fastener and larger forces acting on the supporting means in a direction perpendicular to the body and away from the body can be carried without causing any movement of the device. The second fastener can comprise a body engaging element, preferably having a soft surface.

In another embodiment the body attached element of the fastening means comprises an elongated rectangular pad. A first side of the pad is provided with an adhesive that is suitable for securing the fastening means to the skin.

In yet another embodiment the fastening means is provided with two separated fasteners that are located substantially at the same distance from the supporting means. By using two separated fasteners larger forces can be received while at the same time maintaining the appliance and device in the correct position. Also combinations of the above described embodiments are possible within the scope of the present invention.

The connecting element of the fasteners can be formed as fabric hook-and-loop fasteners. One side of the fasteners can be provided with an adhesive suitable for securing the fastener to the skin and forming the connecting element. The body attached element can include metal or ceramic implants that integrate with bone by osseous integration. A suitable location for the integration is the sternum. In such embodiments it is normally sufficient to provide a single fastening location, since a very firm attachment can be ensured. The connecting element again can be fabric hook-and-loop fasteners. Generally, the connecting element can comprise magnets, fabric hook-and-loop fasteners as set out above, snap connections and other functionally similar devices.

Preferably the device is formed by a flexible and/or plastic material that will allow adjustment of the device to the factual physical circumstances. The device can be bent to a suitable shape and then be maintained in that form while maintaining some resilience. In some embodiments the complete device is formed by such a flexible material and in other embodiments at least the supporting means is made flexible. An optional intermediate section also can be flexible or adjustable depending on the extension of the section and on the depth of the stoma. Where the intermediate section is made flexible other sections of the device can be formed more or completely rigid.

The supporting means can be formed by the same material as the fastening means. However, different requirements and working conditions of the supporting means and the fastening means normally lead to a selection of different materials. Where different materials are used for the supporting means and the fastening means, respectively, the supporting means is attached to the fastening means by suitable means such as glue or through insert moulding or by any other suitable method.

In an alternative embodiment the supporting means is divided into two separate elements that are releasably attached to each other. The separate elements comprise means for ensuring that the elements will attach in a well defined mutual position.

In a specific embodiment the supporting means comprises a first magnet and the fastening means comprises a second magnet cooperating with the first magnet. The fastening means further comprises a body attached slip and a connecting element. The body attached slip and the connecting element are releasably connected to each other.

An advantage with this alternative embodiment is that the supporting means readily can be removed, for instance for cleaning, and then replaced at a very well defined position since the magnets will snap into engagement with each other. Furthermore, possible difficulties in finding the appropriate position when the connecting element is connected to the body attached slip can be avoided since the connecting element can remain fastened to the body attached slip also when the supporting means is removed.

BRIEF DESCRIPTION OF THE DRAWINGS

In order that the manner in which the above recited and other advantages and objects of the invention are obtained will be readily understood, a more particular description of the invention briefly described above will be rendered by reference to specific embodiments thereof which are illustrated in the appended drawings.

Understanding that these drawings depict only typical embodiments of the invention and are not therefore to be considered to be limiting of its scope, the invention will be described and explained with additional specificity and detail through the use of the accompanying drawings in which:

FIG. 2 is a perspective view showing the device in FIG. 1, FIG. 3 is a top view of the embodiment in FIG. 2, FIG. 4 is a side view of the embodiment in FIG. 2, FIG. 5 shows schematically an alternative embodiment of a device in accordance with the invention, FIG. 6 is a side view of the embodiment in FIG. 5, FIG. 7 shows schematically a further alternative embodiment of a device in accordance with the invention, FIG. 8 shows schematically a further alternative embodiment of a device in accordance with the invention.

DETAILED DESCRIPTION

Figure 1:
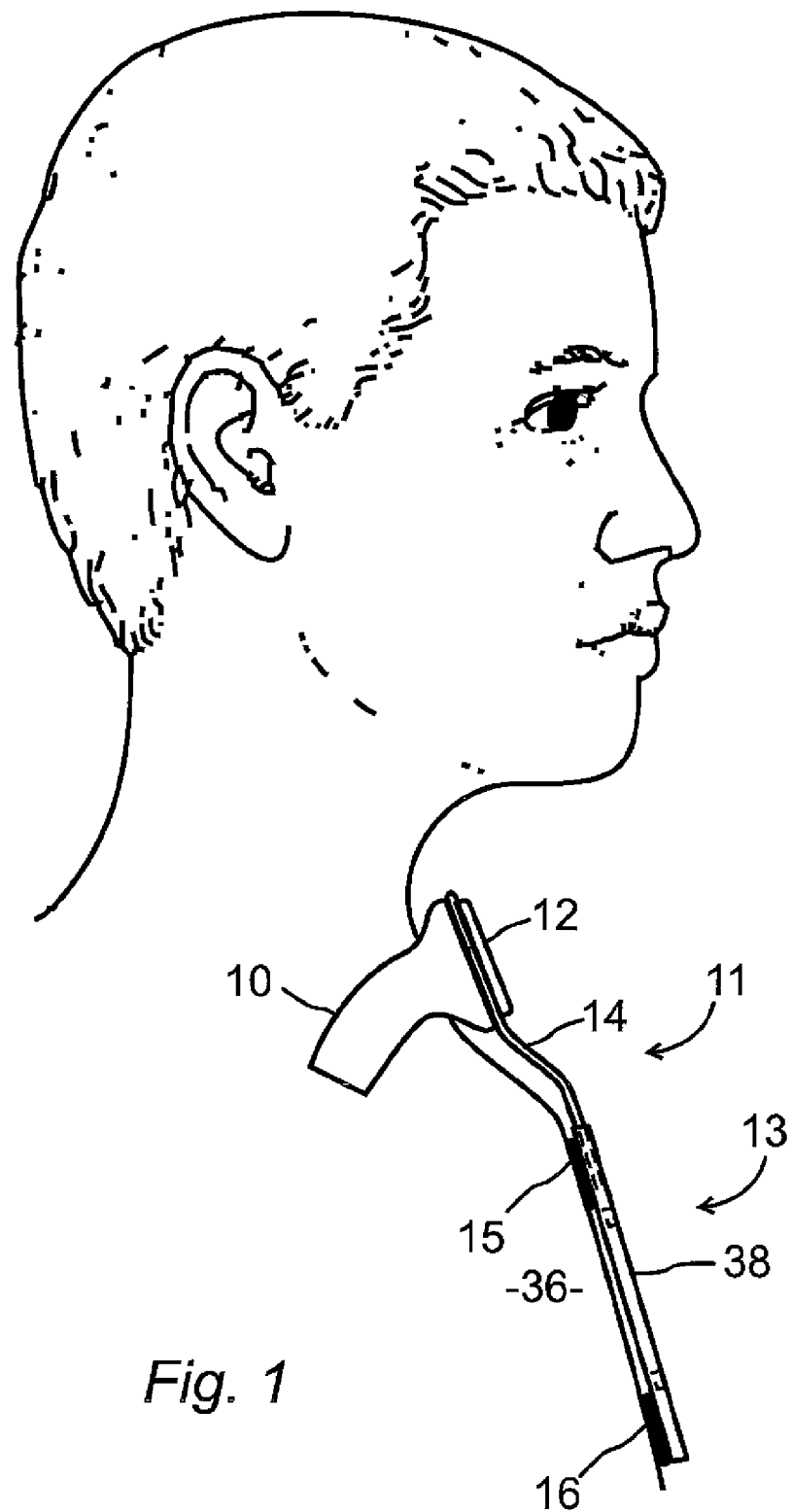
FIG. 1 shows schematically elements of a basic embodiment in accordance with the invention arranged in position on a patient.

In FIG. 1 a tracheostomized person carries a tracheal cannula 10 with a device 11 in accordance with the invention. The device 11 is provided with supporting means 12 and fastening means 13. The supporting means 12 supports the tracheal cannula 10 at the opening of a stoma. In the embodiment shown in FIG. 1 the supporting means 12 extends over an intermediate section 14, comprising a first bend adjacent to the supporting means 12 and a second bend adjacent to the fastening means, the bends being oriented in opposite directions. After the bends the supporting means is attached to the fastening means 13. As a result of the two bends the fastening means 13 is displaced a distance from the supporting means 12 and engages the body or more specifically the chest 36 of the patient below the throat. The distance between the supporting means 12 and the fastening means 13 normally exceeds the opening diameter of the stoma. Since the intermediate section 14 can be very slender the device 11 as a whole will be very discrete.

The fastening means 13 engages the chest at a first location 15 adjacent to the second bend and at a second location 16 which is more distant from the second bend. At the first location 15 the fastening means is provided with connecting elements formed as fabric hook-and-loop fasteners that are attached to a holder 38. One side of a first fastener is provided with an adhesive suitable for securing the fastener to the skin while a first side of a second fastener is attached to the device 11. The fabric is attached to a second side of the first fastener and the second fastener, respectively. At the second location 16 it is sufficient to provide the holder 38 with a soft pad.

The length of the holder 38 and two spaced apart locations for attaching the fastening means to the body of the patient ensures that no rotating movement of the device will occur if forces turned outward are applied on the tracheal cannula 10. As a result the supporting means will be maintained in position and no undesired movement of the cannula will take place.

As shown in FIG. 2 the device 11 comprises supporting means 12 and a fastening means 13. The supporting means in this embodiment is a metal wire extending by two legs 17 from the fastening means. The two legs are connected by a circle section 18 which supports the medical appliance. The legs 17 also form an intermediate section 14 of the device that connects the supporting means 12 and a T-shaped base plate 23 forming the holder of the fastening means 13. The base plate is elongated and has a proximal end connecting the intermediate section and a distal end. The intermediate section 14 provides a sufficient distance between the supporting means 12 and the fastening means 13 for preserving the skin around the stoma site. The intermediate section 14 also will make it possible to conceal the fastening means 13 under clothing.

The fastening means 13 comprises three pads 19a-19c. A first pad 19a and a second pad 19b are arranged on the fastening means where the legs 17 are connected to the fastening means while a third pad 19c is provided on a distal part of the fastening means in relation to the intermediate section. At least the pads 19a and 19b comprise fabric hook-and-loop fasteners that are attached to the T-shaped fastening means.

The third pad 19c will provide a soft skin engaging spot and may be formed by a soft material.

For each pad 19a and 19b there can be provided an associated slip 20, one side of which comprising an adhesive for the skin and an opposite side thereof optionally holding an interacting piece or member 22 of fabric hook-and-loop fastener. The slips 20 will be attached to the skin of the patient at locations that are readily concealed with clothes. Preferably, the slips 20 are attached to the sternum. An attachment position below the throat ensures that the device will not move when the user of the device turns his head. Such a position also will facilitate the attachment of the slips 20 since the sternum forms a firm support. The slips and the pads together form the connecting element.

The legs 17 can be adjusted to compensate for different physical properties of the patient and the depth of the stoma. As shown below the intermediate section also can be formed with different displacements to be adapted to specific physiological conditions. The fastening means is also formed with a plurality of bending zones 21 that will allow further adjustments. In the embodiment shown in FIG. 2 the T-shaped base plate 23 is made of a polymer material, such as polycarbonate.

The displacement between the supporting means 12 and the fastening means 13 is shown in more detail in FIG. 3 and FIG. 4. In FIG. 3 a distance A separates the fastening means 13 from the supporting means 12, in this embodiment a circle section wire. The orientation of the device 11 in FIG. 3 corresponds to the orientation of the device in use on a patient and it is clear that complete fastening means readily can be concealed by clothes because of the distance A below the supporting means. The distance A may vary considerably in different embodiments and depending on physical conditions. In embodiments where A is around 10 mm the skin close to the stoma is spared and the fastening means is readily concealed.

Since the fastening means 13 comprises fastening elements at a first distance A, corresponding to the first location 15, and fastening elements or preferably body engaging means at a second distance B, corresponding to the second location 16, from the supporting means, a very firm and stable attachment of the device on the body of the patient can be obtained. The shape and size of the circled section 18, the legs 17 and distance A are determined by the shape and size of the medical appliance and to some extent by the physical dimensions of the patient. In this embodiment the pads 19a and 19b are provided for attaching the fastening means to the body of the patient.

The bending zones 21 are provided at suitable locations to allow further adjustments of the shape of the fastening means by simple bending the base plate at these locations. The bending zones 21 may comprise areas of thinned out or weakened base material.

While the distance A relates to a displacement of the fastening means from the supporting means in the direction along the body of a person using the device a distance D relates to a displacement in depth between the fastening means and the supporting means, as shown in FIG. 4. The distance D is determined by the depth and type of the stoma. Preferably there are provided devices 11 of different sizes, also including different distances A, B and D.

In the embodiment shown in FIG. 5 and FIG. 6 the fastening means 13 comprises a longitudinally extending, or rectangular, base plate 24 that replaces the T-shaped plate as described above and forming the holder 38 of the device 11. Also in this embodiment the base plate is elongated and has a proximal end connecting the intermediate section and a distal end. The supporting means 12 corresponds to the supporting means described above. In this embodiment a metal or ceramic implant 25 that integrates with bone by osseous integration is utilized as a body attachment element. The implant is a screw comprising a first magnet 26 arranged at the head of the screw. A second magnet 27 is provided on the rectangular base plate 24 and will cooperate with the first magnet 26 to maintain the device in a desired position. The first magnet 26 and the second magnet 27 form the connecting element that will allow all elements of the device 11 except for the implant 25 to be readily removed from the body. The screw can be replaced by other implant devices.

Also in this embodiment it may be appropriate to provide the base plate with bending zones 21 to allow final adjustments. Furthermore, devices can be produced with different sizes and different distances D to be adapted to the patient. The supporting means comprises a U-shaped section 39 extending from an arm 40 which is connected to the base plate 24 by insert moulding.

The embodiment in FIG. 7 comprises a device 28 where a supporting means 29 and a fastening means 30 are integrated into a curved base plate 34 made by a flexible material. The fastening means 30 comprises a first part 31 of a snap connecter while a cooperating second part 32 of the snap connector is attached to an implant 33. The length of the base plate 24 and 34, respectively, corresponding to the distance between the proximal end and the distal end of the base plate will ensure that no rotating movement of the base plate around implant screw as illustrated by arrow R will occur when a force F acts on the supporting means. The force F can be rather substantial, for instance when the supporting means supports a voice prosthesis or a speech valve. Also other embodiments as shown above with reference to FIG. 1 to FIG. 5, FIG. 8 and other embodiments in accordance with the invention will prevent rotation in the direction of arrow R.

Different shapes of the base plate are indicated by dash and dot lines in FIG. 7. Similar shapes can be provided also with other embodiments of the base plate and intermediate section. The embodiment shown in FIGS. 2 and 3 can be made completely flat or with other suitable shapes. The distance D in FIG. 6 may vary from 0 mm to at least 25 mm.

The embodiment in FIG. 8 substantially corresponds to the embodiment of FIG. 5 and all corresponding elements have the same references. The two legs 17 in this embodiment are connected to a base plate 35 by gluing at two joints 37.

Figure 9:
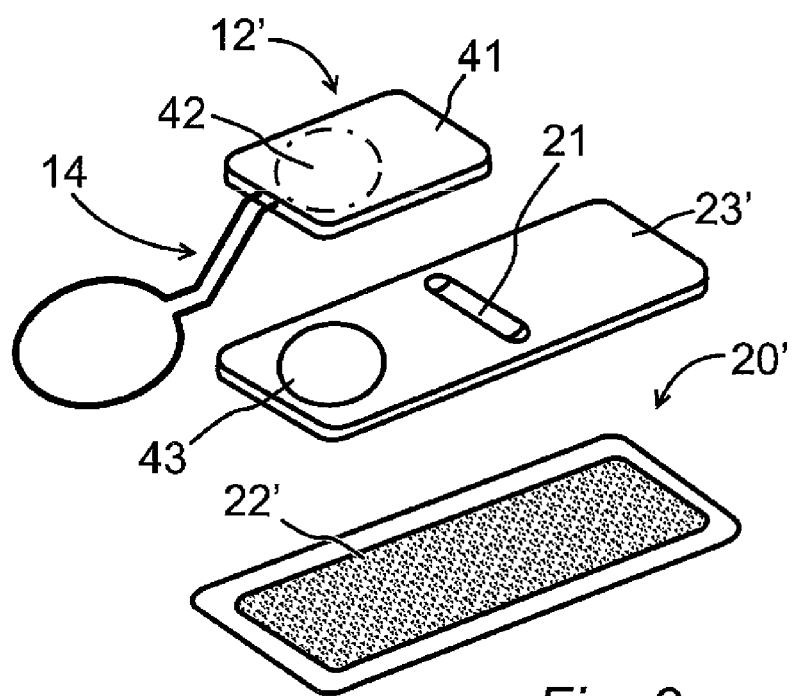
FIG. 9 is an exploded view showing a further alternative embodiment of a device in accordance with the invention.

In the embodiment shown in FIG. 9 a modified supporting means 12' and a modified base plate 23' are used. The modified base plate 23' is on one flat side provided with one member of a fabric hook-and-loop fastener. An interacting member 22' of the hook-and-loop fastener is provided on an extended body attached slip 20'. By pressing the hook-and-loop fastener of the body attached slip 20' into engagement with the hook-and-loop fastener of the modified base plate 23' a very firm connection can be achieved.

As shown in FIG. 9 the intermediate section 14 extends into a connecting element formed as a holding plate 41. The holding plate 41 is rectangular and somewhat smaller than the rectangular modified base plate 23'. It is possible also to use other shapes of the base plate and the holding plate and also more similar sizes. The holding plate 41 supports a first positioning magnet 42 that can be embedded in or attached to the holding plate 41.

A corresponding second positioning magnet 43 is embedded in or attached to the modified base plate 23'. The first and the second magnet will ensure that the modified supporting means 12' returns to a well defined position in relation to the modified base plate 12' after being removed for some reason because the magnets will be attracted to each other.

The first positioning magnet 42 also can be supported directly in one end of the intermediate section 14. In this case the holding plate 41 can be omitted.

It should be noted that different forms of base plates, fasteners and supporting means as shown above can be combined in other ways than set out above as may be found appropriate. For instance, a T-shaped base plate can be combined with a fastening means glued thereon. A single fastening element can comprise a set of fabric hook-and-loop fasteners.

In accordance with the invention the device also will prevent bulging around the speech valve when speaking because the fastening location or locations are present on the chest of the patient below the stoma. The firm engagement of the medical appliance in the stoma also will accomplish a good sealing between the appliance and the stoma. This is a major advantage especially when the appliance is combined with a speech valve.

While certain illustrative embodiments of the invention have been described in particularity, it will be understood that various other modifications will be readily apparent to those skilled in the art without departing from the scope and spirit of the invention. Accordingly, it is not intended that the scope of the claims appended hereto be limited to the description set forth herein but rather that the claims be construed as encompassing all equivalents of the present invention which are apparent to those skilled in the art to which the invention pertains.

The invention claimed is:

1. A device that supports and retains a tracheal cannula or a stoma stent in a neck of a patient, comprising;
   a support, a holder and an intermediate section positioned between the support and the holder such that the support and the holder are spaced apart;
      wherein the support is positionable to overlap a stoma in a neck of a patient without contacting the neck while supporting a medical appliance in the stoma; and
      wherein the holder extends longitudinally from the intermediate section so as to be positionable over a chest of the patient and includes a first fastener and a second fastener, wherein the first fastener is removably attached to a body attachable element that is adherable to the chest of a patient and wherein the second fastener is separately engagable with the patient's chest;
      wherein the first fastener is spaced from the support by a first distance and the second fastener is spaced from the support by a second distance, the second distance being larger than the first distance, and wherein the first fastener does not overlap with the second fastener.

2. The device of claim 1 wherein the first fastener removably attaches to the body attachable element through a hook and loop connection.

3. The device of claim 1 wherein the first fastener removably attaches to the body attachable element through a magnet connection.

4. The device of claim 1 wherein the first fastener removably attaches to the body attachable element through a snap connection.

5. The device of claim 1 wherein the holder comprises a flexible material.

6. The device of claim 5 wherein the holder comprises a soft pad.

7. The device of claim 1 wherein the support comprises a flexible material.

8. The device of claim 7 wherein the support comprises a flexible wire.

9. The device of claim 8 wherein the flexible wire is configured as a circle.

10. The device of claim 1 wherein both the support and the intermediate section comprise a flexible wire.

11. The device of claim 10 wherein the flexible wire extends from the holder as two legs and a circle connecting the two legs.

12. The device of claim 1 wherein the first fastener comprises two spaced apart fasteners each correspondingly attached to one body attachable element.

13. The device of claim 1 wherein the intermediate section extends from the support whereby the device is usable by the patient without the intermediate section contacting the patient's neck.

* * * * *